US012747211B2

(12) United States Patent
Murugan et al.

(10) Patent No.: US 12,747,211 B2

(45) Date of Patent: Sep. 29, 2026

(54) METHODS OF MAKING NICOTINIC ACID DERIVATIVES

(71) Applicant: SYNGENTA CROP PROTECTION AG, Basel (CH)

(72) Inventors: Ramiah Murugan, Indianapolis, IN (US); Colin Smith, Roachdale, IN (US); Roger W. Tharp-Taylor, Noblesville, IN (US)

(73) Assignee: SYNGENTA CROP PROTECTION AG, Basel (CH)

( * ) Notice: Subject to any disclaimer, the term of this patent is extended or adjusted under 35 U.S.C. 154(b) by 457 days.

(21) Appl. No.: 18/032,842

(22) PCT Filed: Oct. 22, 2021

(86) PCT No.: PCT/US2021/056198

§ 371 (c)(1),
(2) Date: Apr. 20, 2023

(87) PCT Pub. No.: WO2022/087373

PCT Pub. Date: Apr. 28, 2022

(65) Prior Publication Data

US 2024/0002341 A1 Jan. 4, 2024

Related U.S. Application Data

(60) Provisional application No. 63/104,954, filed on Oct. 23, 2020.

(51) Int. Cl.

*C07D 213/80* (2006.01)
*C07D 213/803* (2006.01)
*C07D 309/28* (2006.01)

(52) U.S. Cl.

CPC ....... *C07D 213/80* (2013.01); *C07D 213/803* (2013.01); *C07D 309/28* (2013.01)

(58) Field of Classification Search

CPC . C07D 213/80; C07D 213/803; C07D 309/28
See application file for complete search history.

(56) References Cited

U.S. PATENT DOCUMENTS

| | | | |
|---|---|---|---|
| 4,873,250 | A | 10/1989 | Hufford et al. |
| 7,723,522 | B2 | 5/2010 | Kuwabara et al. |
| 9,481,650 | B2 | 11/2016 | Trussardi |
| 2005/0171355 | A1 | 8/2005 | Kuwabara et al. |

FOREIGN PATENT DOCUMENTS

| | | | | |
|---|---|---|---|---|
| CN | 104 781 236 | A | | 7/2015 |
| CN | 110 878 044 | A | | 3/2020 |
| EP | 1 559 711 | A1 | | 8/2005 |
| JP | 2005-213239 | A | | 8/2005 |
| WO | 2015/0197530 | | | 12/2015 |
| WO | 2018/055640 | A1 | | 3/2018 |
| WO | 2020/0025574 | | | 2/2020 |
| WO | 2020025574 | | * | 2/2020 |

OTHER PUBLICATIONS

Tilekar, 2017, Tetrahedron: Asymmetry, vol. 28, 153-161. (Year: 2017).*
Wang, Org Lett, vol. 10, No. 12, 2008, 2561-2564. (Year: 2008).*
Eiden, Arch Pharm, vol. 22, 617-627, 1989. (Year: 1989).*
International Search Report and Written Opinion for PCT/US2021/056198 dated Mar. 4, 2022.
Mase et al. "Intermolecular Michael Reaction of Alehydes with alpha, beta-Unsaturated Esters", Science of Synthesis: Asymmetric Organocatalysis. Jan. 2012, 156, 4 pages.
PubChem-SID-370447587, Mody Date: May 25, 2015, p. 2.
Moustafa et al. "Organobase-catalyzed three-component reactions for the synthesis of 4H-2-aminopyrans, condensed pyrans and polysubstituted benzenes", Beilstein J. Org. Chem. 2015, 10, pp. 141-149.
Extended European Search Report issued in European Patent Application No. EP 21883963.7, mailed Jul. 26, 2024.
Tilekar, et al., "One-pot' organocatalyzed enantioselective synthesis of highly functionalized 3,4,5,6-tetrasubstituted dihydropyrans by sequential Knoevenagel condensation/Michael addition and hemiacetalization", Tetrahedron Asymmetry, 28(1), pp. 153-161, 2017.
Wang, et al., "Enantioselective Assembly of Substituted Dihydropyrones via Organocatalytic Reaction in Water Media", Organic Letters, vol. 10. Issue 12, pp. 2561-2564, 2008.
Roy, et al., "The Hemetsberger-Knittel Synthesis of Substituted 5-, 6-, and 7-Azaindoles", Synthesis, (16), pp. 2751-2757, 2005.
Majee, et al., "Domino reaction of cyclic sulfamidate imines with Morita-Baylis-Hillman acetates promoted by DABCO: a metal-free approach to functionalized nicotinic acid derivatives", Organic & Biomolecular Chemistry, 2017.
Search report from CAS STNext exported on Jul. 2, 2025; 68 pages.
Chinese Patent Office Action dated Jul. 8, 2025, English Translation; 6 pages.
Chinese Patent Office Action dated Nov. 20, 2025, English Translation; 6 pages.
Japanese Patent Office Action dated Jan. 15, 2026, English Translation; 3 pages.
Japanese Search Report dated Jul. 31, 2025, English Translation; 63 pages.
Niu, et al., "The efficient enantioselective synthesis of dihydropyrans via organocatalytic Michael addition reactions", Tetrahedron: Asymmetry, vol. 25, pp. 796-801, 2014.
Ueyama, et al., "Nonpeptide angiotensin II receptor antagonists. I. Synthesis and biological activity of pyridine derivatives", Chem Pharm Bull, vol. 42(9), pp. 1841-1849, 1994.

(Continued)

*Primary Examiner* — D Margaret M Seaman

(74) *Attorney, Agent, or Firm* — BakerHostetler; Toni-Junell Herbert

(57) ABSTRACT

This disclosure relates to processes for preparing nicotinic acid derivatives that are useful in the chemical arts, such as in the manufacture of pharmaceutical products or agrochemicals. In particular, the present disclosure pertains to novel processes for preparing certain nicotinic acid derivatives.

15 Claims, No Drawings

(56) References Cited

OTHER PUBLICATIONS

Pan, et al., "Isolation and synthesis of antiproliferative eupolauridine alkaloids of Ambavia gerardii from the Madagascar Dry Forest", Journal of Natural Products, vol. 74 (5), pp. 1169-1174, 2011.
Kiss, et al., "Efficient Synthesis of 2 -(Trifluoromethyl) nicotinic Acid Derivatives from Simple Fluorinated Precursors", Organic Letters, vol. 10 (9), pp. 1835-1837, 2008. Supporting Information.
Yamauchi, et al., "Synthesis of alkyl 2—phenylnicotinates", Journal of Heterocyclic Chemistry, vol. 34, pp. 93-96, 1997.
Raja, et al., "A heavy metal-and oxide-free, one pot synthesis of pyridine and fused pyridine based on a Lewis acid-catalyzed multicomponent reaction", Chemical Communications, vol. 50, pp. 12270-12272, 2014.

* cited by examiner

METHODS OF MAKING NICOTINIC ACID DERIVATIVES

CROSS REFERENCE TO RELATED APPLICATIONS

This application is a U.S. national stage application under 35 U.S.C. § 371(b) of International Application No. PCT/US2021/056198, filed Oct. 22, 2021, which claims priority to the U.S. Patent Application No. 63/104,954, filed on Oct. 23, 2020, the disclosures of both of which are hereby expressly incorporated by reference in their entirety.

TECHNICAL FIELD

This disclosure relates to processes for preparing nicotinic acid derivatives that are useful in the chemical arts, such as in the manufacture of pharmaceutical products or agrochemicals. In particular, the present disclosure pertains to novel processes for preparing certain nicotinic acid derivatives.

BACKGROUND

The manufacture of pharmaceutical products and agrochemical products is a complex and heavily regulated field of industry. Among the many considerations taken into account in the manufacture of pharmaceutical products and agrochemical products are aspects such as cost of raw starting materials, cost of processing of intermediates and products, efficiency of chemical synthesis, ease of purification and handling, and the like. As a result of the many forces at play in the manufacture of pharmaceutical products and agrochemical products, manufacturers expend significant resources to optimize their chemical synthesis processes and intermediates.

For example, 2-trifluoromethylnicotinc acid and its carboxylic acid derivatives such as esters, nitrile and amides have been used both as pharmaceutical product intermediates as well as agrochemical product intermediates. For example, 2-trifluoromethylnicotinic acid has been used as an intermediate in the preparation of fungicides (See, Shigehara, I.; Nakajima, T.; Nishide, H.; Tanimura, T., JP 03081263 A (Apr. 5, 1991)); heterocyclic carboxamides made from 2-trifluoromethylnicotinic acid have also been used as fungicides (See, Mansfield, D. J.; Rieck, H.; Geul, J. N., et al., EP 1449841 A1 (Aug. 25, 2004)); heteroaryl carboxamides made using 2-trifluoromethylnicotinic acid and aniline derivatives have also been used as fungicides (See, Gewehr, M.; Dietz, J.; Grote, T., et al., WO 2006097490 A1 (Sep. 21, 2006)); 2-trifluoromethylnicotinic acid has been used as an intermediate in the synthesis COMT (catechol-O-methyltransferase) inhibitors which are used in the treatment of nervous system disorders such as Parkinson's disease in the pharmaceutical industry (See, Learmonth, D.; Kiss, L.; Leal Palma, P., et al., WO 2007013830 A1 (2007)); 2-trifluoromethylnicotinic acid amide derivatives have been used in the synthesis of agrochemical products used against nematodes (See, Loiseleur, O.; Jeanguenat, A.; Mondleve, R. J. G., WO 2015004091 A1 (Jan. 15, 2015)); 2-trifluoromethylnicotinic acid has been used in the synthesis of pyrido-pyridines as well as pyrimidino-pyridines for use as herbicides in the agrochemical industry (See, Carter, N. B., et al., WO 2017162522 A1 (Sep. 28, 2017); WO 2017162521 A1 (Sep. 28, 2017); WO 2017162524 A1 (Sep. 28, 2017)).

Herbicidal use of amides derived from 2-trifluoromethylnicotinic acid has been reported (See, Xu, 1., CN 108623518 A (Oct. 9, 2018)). The use of 2-trifluoromethylnicotinic acid in the synthesis of final agrochemical products used as pesticides has been also reported. The active compounds have other heterocycles on the nitrogen substituent of the amide derivative of 2-trifluoromethylnicotinic acid (See, Décor, A.; Lishchynskyi, A., et al., WO 2018108791 A (Jun. 21, 2018); Décor, A.; Fischer, R., et al., WO 2019105875 A1 (Jun. 6, 2019)). The use of N-substituted amides of 2-trifluoromethylnicotinic acid as nematicides or fungicides has also been reported. The N-substituent also has a four membered ring along with a 2,4-dichlorophenyl group. (Hone, I.; Jones, I. K., WO 2019158476 A1 (Aug. 22, 2019)).

Various methods have been used to prepare nicotinic acid derivatives. For example, the preparation of 2-trifluoromethylnicotinic acid has been accomplished using both ring synthesis and chemical transformation on a pyridine ring. One challenge related to the pyridine ring chemical transformation has been the introduction of the $CF_3$ group. For this various reagents have been used, and usually involve displacement of a halogen. Exemplary options for this transformation are as follows depicted in a retrosynthetic wheel diagram.

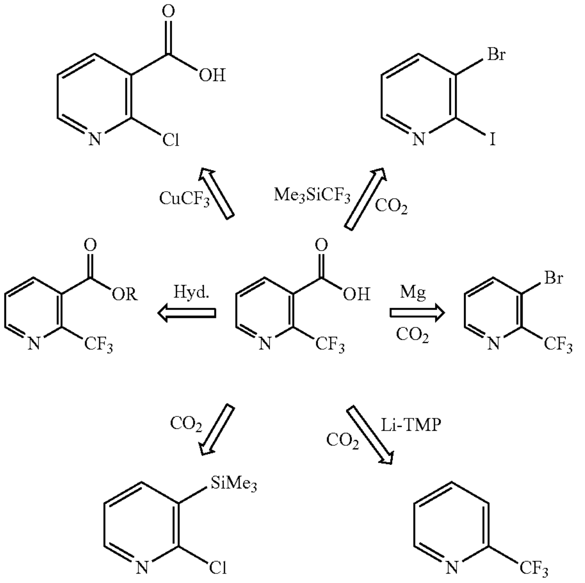

A process starting with 2-chloronicotinic acid and displacing the chlorine atom by a $CF_3$ anion has been used for the synthesis of 2-trifluoromethylnicotinic acid. The trifluoromethyl anion has been generated using iodo-trifluoromethane and copper (See, Shigehara, I.; Nakajima, T.; Nishide, H.; Tanimura, T., JP 03081263 A (Apr. 5, 1991)).

An alternative process starting from 2-trifluoromethylpyridine, made using $CF_3Cu$ and 2-chloropyridine using lithium 2,2,6,6-tetramethyl-piperidide as the base followed by quenching with carbon dioxide has also been used to prepare 2-trifluoromethylnicotinic acid. In this process, the formation of 4-isomer, 2-trifluoromethylisonicotinic acid has been observed as a byproduct (Taylor, R. T., Reagents for Organic Synthesis, 2001).

2-Trifluoromethylnicotinic acid has also been synthesized using 2-chloro-3-trimethylsilylpyridine as the starting material and the reagent $CF_3SiMe_3$ as a transfer reagent (Cottet, F., et al., European Journal of Organic Chemistry, 1559, 2003).

Alternatively, forming a Grignard reagent from 2-trifluoromethyl-3-bromopyridine by contacting with magnesium followed by quenching with carbon dioxide has been used in the synthesis of 2-trifluoromethylnicotinic acid (Didiuk, M. T. et al., Bioorganic & Medicinal Chemistry Letters, 19, 4555, 2009).

Starting from either 2,3-dibromopyridine or 2-iodo-3-bromopyridine and the reagent $CF_3SiMe_3$, the product 2-trifluoromethylnicotinic acid has also been synthesized (Li, B. et al., Synlett, 2133, 2010).

Also, the hydrolysis of 2-trifluoromethylnicotinic acid esters have been reported for the synthesis of 2-trifluoromethylnicotinic acid. (Sharma, S.; Dhaka, P.; Jangid, D.; Kumar, K.; Anand, R., Ind. Pat. Appl. 201611032457 (Mar. 23, 2018); WO 2018055640 (Mar. 29, 2018)).

Two of the approaches, one dealing with ring transformation and the other dealing with ring synthesis are compared, and are shown below.

V

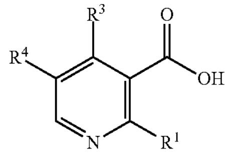

wherein each of $R^1$, $R^3$, and $R^4$ are as defined herein; useful as intermediates in the preparation of chemical products, such as pharmaceuticals and agrochemicals.

In another aspect, the present disclosure provides a compound of the formula III

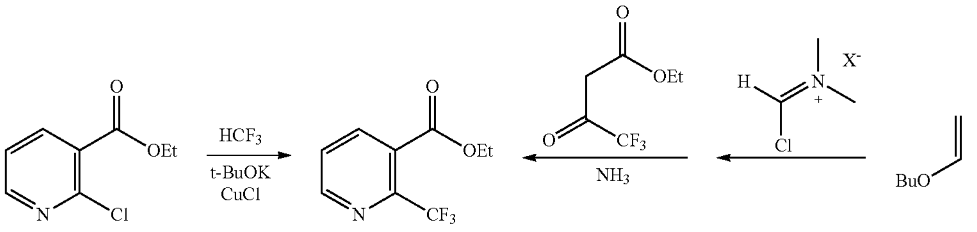

For example, a reported ring transformation approach starts with 2-chloronicotinic acid an expensive starting material, and a nucleophilic displacement of chlorine atom using trifluoromethyl anion is performed. The generation of trifluoromethyl anion has been done from fluoroform using stoichiometric amount of base potassium t-butoxide and copper chloride (Lishchynskyi, A.; Novikov, M. A.; Martin, E.; Escudero-Adan, E. C.; Novak, P.; Grushin, V. V., Journal of Organic Chemistry 78, 11126, 2013).

In the case of ring synthesis, trifluoroacetic acid derivatives have been used for the introduction of the CF3 group on the pyridine ring. In one reported ring synthesis approach, a Vilsmeier reaction is carried out on vinyl butyl ether to make the 1,3-diformylpropane equivalent compound, which then reacted with trifluoro-acetoacetic acid ester compound to form the five carbon chain intermediate. This five carbon intermediate is cyclized in presence of ammonia to form the final product, 2-trifluoromethylnicotinic acid ester (Kiss, L. E.; Ferreira, H. S.; Learmonth, D. A., Organic Letters 10, 1835, 2008).

The reported synthetic methods to make nicotinic acid derivatives, such as 2-trifluoromethylnicotinic acid, have been either non-economical and/or generate too much waste to become a commercially relevant manufacturing process for the larger volumes required in manufacture of pharmaceutical products and agrochemical products. Accordingly, there remains a need for improved processes and intermediates for use in the preparation of nicotinic acid derivatives, such as 2-trifluoromethylnicotinic acid.

SUMMARY

In one aspect, the present disclosure provides a process for preparing a nicotinic acid derivatives of the formula V

III

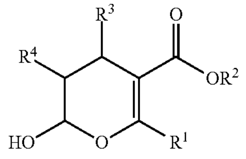

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl;

$R^2$ is a $C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl.

In another aspect, the present disclosure provides a process for preparing a compound of the formula III

III

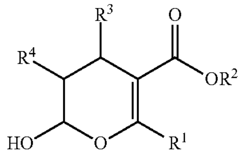

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl;

$R^2$ is a $C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl.

comprising contacting a compound of the formula I

I

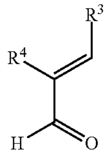

wherein each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; with a compound of the formula II

II

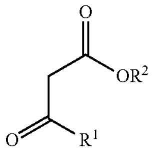

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; and $R^2$ is a $C_1$-$C_8$ alkyl; in the presence of a base.

In another aspect, the disclosure provides a process for preparing a nicotinic acid derivative of the formula V

V

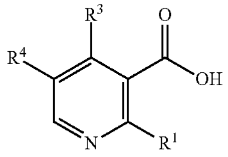

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl;

comprising i. contacting a compound of the formula I

I

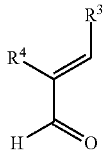

wherein each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; with a compound of the formula II

II

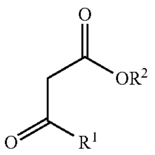

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; and $R^2$ is a $C_1$-$C_8$ alkyl; in the presence of a base to provide a compound of the formula III

III

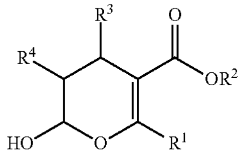

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl;

$R^2$ is a $C_1$-$C_8$ alkyl; and/or each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; and/or ii. contacting a compound of the formula III

III

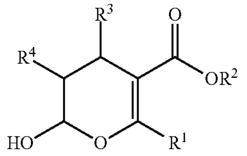

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl;

$R^2$ is a $C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; with an oxidizing agent and an additive to provide a compound of the formula IV

IV

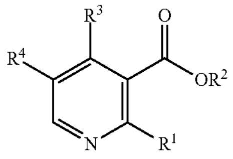

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl;

$R^2$ is a $C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C$-$C_8$ alkyl$)_2$, or —$SC_1$-$C_8$ alkyl; and optionally further comprising iii. contacting the compound of the formula IV

IV

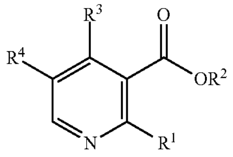

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl;

$R^2$ is a $C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; with a base to provide a compound of the formula V

V

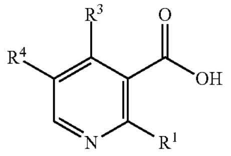

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl.

Additional embodiments, features, and advantages of the disclosure will be apparent from the following detailed description and through practice of the disclosure. The compounds of the present disclosure can be described as embodiments in any of the following enumerated clauses. It will be understood that any of the embodiments described herein can be used in connection with any other embodiments described herein to the extent that the embodiments do not contradict one another.

1. A compound of the formula

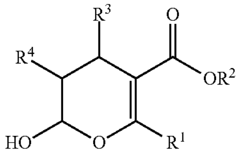

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl;

$R^2$ is a $C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl.

2. The compound of clause 1, wherein $R^1$ is methyl, trifluoromethyl, or difluoromethyl.

3. The compound of clause 1 or 2, wherein $R^4$ is H, methyl, ethyl, n-propyl, i-propyl, or allyl.

4. The compound of any one of the previous clauses, wherein $R^3$ is H, methyl, ethyl, n-propyl, i-propyl, or allyl.

5. The compound of any one of the previous clauses, wherein $R^2$ is methyl, ethyl, n-propyl, or i-propyl.

6. The compound of any one of the previous clauses, selected from the group consisting of

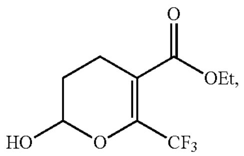 , 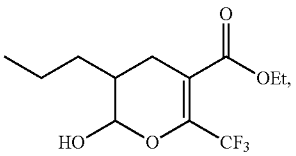 , 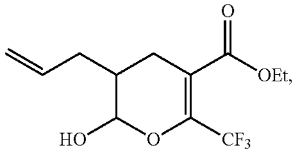 , 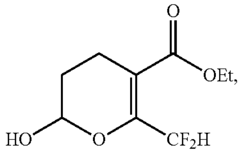 ,

-continued

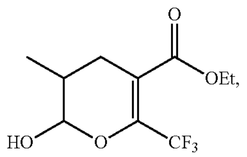 , and 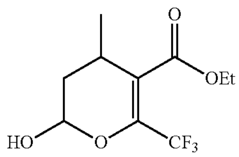

7. A process for preparing a compound of the formula

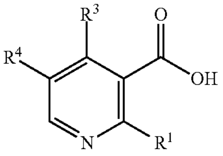

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in C-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl;

comprising i. contacting a compound of the formula

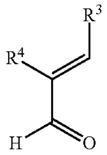

wherein each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; with a compound of the formula

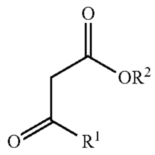

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; and $R^2$ is a $C_1$-$C_8$ alkyl; in the presence of a base to provide a compound of the formula

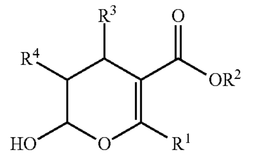

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl;

$R^2$ is a $C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl.

8. A process for preparing a compound of the formula

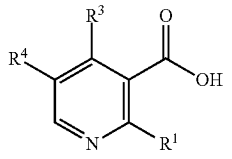

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl;

comprising ii. contacting a compound of the formula

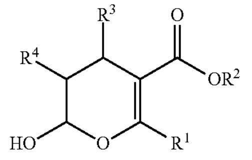

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl;

$R^2$ is a $C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; with an oxidizing agent and an additive to provide a compound of the formula

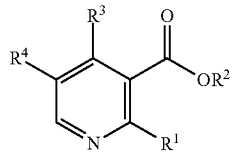

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl;

$R^2$ is a $C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl.

9. A process for preparing a compound of the formula

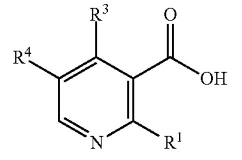

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl;

comprising i. contacting a compound of the formula

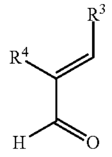

wherein each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; with a compound of the formula

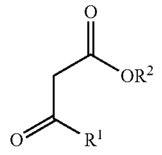

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; and $R^2$ is a $C_1$-$C_8$ alkyl; in the presence of a base to provide a compound of the formula

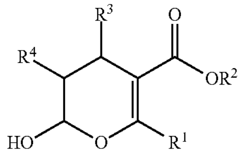

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl;

$R^2$ is a $C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; and ii. contacting a compound of the formula

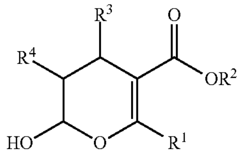

prepared in step (i) with an oxidizing agent and an additive to provide a compound of the formula

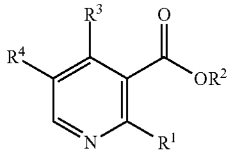

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl;

$R^2$ is a $C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl.

10. The process of any one of clauses 7 to 9, further comprising iii. contacting the compound of the formula

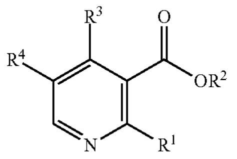

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —O$C_1$-$C_8$ alkyl, —N($C_1$-$C_8$ alkyl)$_2$, or —S$C_1$-$C_8$ alkyl;

$R^2$ is a $C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —O$C_1$-$C_8$ alkyl, —N($C_1$-$C_8$ alkyl)$_2$, or —SC i-$C_8$ alkyl; with a base to provide a compound of the formula

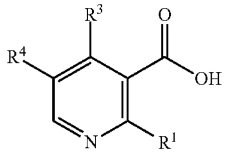

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —O$C_1$-$C_8$ alkyl, —N($C_1$-$C_8$ alkyl)$_2$, or —S$C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —O$C_1$-$C_8$ alkyl, —N($C_1$-$C_8$ alkyl)$_2$, or —S$C_1$-$C_8$ alkyl.

11. The process of any one of clauses 7 to 10, wherein the base in step (i) is an organic base.

12. The process of any one of clauses 7 to 11, wherein the base in step (i) is an amine base.

13. The process of any one of clauses 7 to 12, wherein the base in step (i) is selected from the group consisting of triethyl amine (TEA), tributyl amine, N,N-diisopropyl ethyl amine (DIPEA), N,N,N',N'-Tetramethyl-1,8-naphthalenediamine, 1,8-diazabicycloundec-7-ene (DBU), 1,5-diazabicyclo(4.3.0)non-5-ene (DBN), and 2,6-di-tert-butylpyridine.

14. The process of any one of clauses 7 to 13, wherein step (i) is carried out in the presence of an alcohol solvent.

15. The process of clause 14, wherein the organic solvent step (i) is selected from the group consisting of methanol, ethanol, iso-propanol, n-propanol, n-butanol, iso-butanol, tert-butanol, n-pentanol, sec-pentanol, iso-pentanol, ethylene glycol, methyl isobutyl carbinol, and propylene glycol.

16. The process of any one of clauses 7 to 15, wherein step (i) is carried out by that addition of acrolein to ethyl trifluoro-acetoacetate at a temperature of about 0° C. to about 25° C.

17. The process of any one of clauses 7 to 16, wherein the oxidizing agent in step (ii) is $O_2$ in the presence of a metal catalyst.

18. The process of clause 17, wherein the metal catalyst is selected from the group consisting of copper (I) acetate, copper (I) chloride, copper (I) oxide, manganese (II) acetate, copper (II) acetate, copper (II) chloride, copper (II) oxide, and iron (III) acetate.

19. The process of any one of clauses 7 to 18, wherein the additive in step (ii) is selected from the group consisting of ammonium acetate, ammonium hydroxide, ammonium chloride, ammonium carbonate, and ammonium nitrate.

20. The process of any one of clauses 7 to 19, wherein step (ii) is carried out in an alcohol solvent.

21. The process of clause 20, wherein the organic solvent step (ii) is selected from the group consisting of methanol, ethanol, iso-propanol, n-propanol, n-butanol, iso-butanol, tert-butanol, n-pentanol, sec-pentanol, iso-pentanol, ethylene glycol, methyl isobutyl carbinol, and propylene glycol.

22. The process of any one of clauses 7 to 21, wherein step (ii) is carried out at between about 60° C. to about 280° C.

23. The process of any one of clauses 7 to 22, wherein the base in step (iii) is an inorganic base.

24. The process of clause 23, wherein the base in step (iii) is selected from the group consisting of sodium hydroxide, lithium hydroxide, potassium hydroxide, cesium hydroxide, calcium hydroxide, barium hydroxide, sodium carbonate, ammonium hydroxide, and mangnesium hydroxide.

25. The process of any one of clauses 7 to 24, wherein $R^1$ is methyl, trifluoromethyl, or difluoromethyl.

26. The process of any one of clauses 7 to 25, wherein $R^4$ is H, methyl, ethyl, n-propyl, i-propyl, or allyl.

27. The process of any one of clauses 7 to 26, wherein $R^3$ is H, methyl, ethyl, n-propyl, i-propyl, or allyl.

28. The process of any one of clauses 7 to 27, wherein $R^2$ is methyl, ethyl, n-propyl, or i-propyl.

29. A process for preparing 2-trifluoromethylnicotinic acid comprising i. contacting one or more esters of 4,4,4-trifluoro-3-oxobutanoic acid with acrolein in the presence of a base to provide a compound of the formula

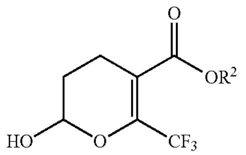

wherein $R^2$ is a $C_1$-$C_8$ alkyl.

30. A process for preparing 2-trifluoromethylnicotinic acid comprising ii. contacting a compound of the formula

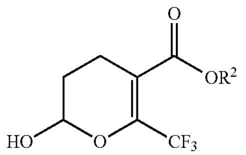

wherein $R^2$ is a $C_1$-$C_8$ alkyl, with an oxidizing agent and optionally an additive to provide one or more esters of 2-trifluoromethylnicotinic acid.

31. A process for preparing 2-trifluoromethylnicotinic acid comprising i. contacting one or more esters of 4,4,4-trifluoro-3-oxobutanoic acid with acrolein in the presence of a base to provide a compound of the formula

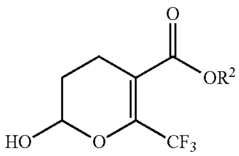

wherein $R^2$ is a $C_1$-$C_8$ alkyl; and ii. contacting a compound of the formula

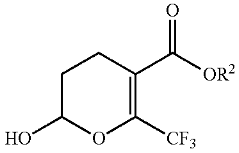

wherein $R^2$ is a $C_1$-$C_8$ alkyl, with an oxidizing agent and optionally an additive to provide one or more esters of 2-trifluoromethylnicotinic acid.

32. The process of any one of clauses 29 to 31, further comprising iii. contacting one or more esters of 2-trifluoromethylnicotinic acid with a base to provide 2-trifluoromethylnicotinic acid.

33. The process of any one of clauses 29 to 32, wherein the base in step (i) is an organic base.

34. The process of any one of clauses 29 to 33, wherein the base in step (i) is an amine base.

35. The process of any one of clauses 29 to 34, wherein the base in step (i) is selected from the group consisting of triethyl amine (TEA), tributyl amine, N,N-diisopropyl ethyl amine (DIPEA), N,N,N',N'-Tetramethyl-1,8-naphthalenediamine, 1,8-diazabicycloundec-7-ene (DBU), 1,5-diazabicyclo(4.3.0)non-5-ene (DBN), and 2,6-di-tert-butylpyridine.

36. The process of any one of clauses 29 to 35, wherein step (i) is carried out in the presence of an alcohol solvent.

37. The process of clause 36, wherein the organic solvent step (i) is selected from the group consisting of methanol, ethanol, iso-propanol, n-propanol, n-butanol, iso-butanol, tert-butanol, n-pentanol, sec-pentanol, iso-pentanol, ethylene glycol, methyl isobutyl carbinol, and propylene glycol.

38. The process of any one of clauses 29 to 37, wherein step (i) is carried out by that addition of acrolein to ethyl trifluoro-acetoacetate at a temperature of about 0° C. to about 25° C.

39. The process of any one of clauses 29 to 38, wherein the oxidizing agent in step (ii) is $O_2$ in the presence of a metal catalyst.

40. The process of clause 39, wherein the metal catalyst is selected from the group consisting of copper (I) acetate, copper (I) chloride, copper (I) oxide, manganese (II) acetate, copper (II) acetate, copper (II) chloride, copper (II) oxide, iron (III) acetate 41. The process of any one of clauses 29 to 40, wherein the additive in step (ii) is selected from the group consisting of ammonium acetate, ammonium hydroxide, ammonium chloride, ammonium carbonate, and ammonium nitrate.

42. The process of any one of clauses 29 to 41, wherein step (ii) is carried out in an alcohol solvent.

43. The process of clause 42, wherein the organic solvent step (ii) is selected from the group consisting of methanol, ethanol, iso-propanol, n-propanol, n-butanol, iso-butanol, tert-butanol, n-pentanol, sec-pentanol, iso-pentanol, ethylene glycol, methyl isobutyl carbinol, and propylene glycol.

44. The process of any one of clauses 29 to 43, wherein step (ii) is carried out at between about 60° C. to about 280° C.

45. The process of any one of clauses 29 to 44, wherein the base in step (iii) is an inorganic base.

46. The process of clause 45, wherein the base in step (iii) is selected from the group consisting of sodium hydroxide, lithium hydroxide, potassium hydroxide, cesium hydroxide, calcium hydroxide, barium hydroxide, sodium carbonate, ammonium hydroxide, and mangnesium hydroxide.

DEFINITIONS

As used herein, the term "alkyl" includes a chain of carbon atoms, which is optionally branched and contains from 1 to 20 carbon atoms, or an alternate range, such as 1 to 8 carbons, or 1 to 6 carbons, and the like." Illustrative alkyl groups include, but are not limited to, methyl, ethyl, n-propyl, isopropyl, n-butyl, isobutyl, sec-butyl, and tert-butyl. It will be appreciated that an alkyl group can be unsubstituted or substituted as described herein. An alkyl group can be substituted with any of the substituents in the various embodiments described herein, including one or more of such substituents.

As used herein, the term "alkenyl" includes a chain of carbon atoms, which is optionally branched, contains from 2 to 20 carbon atoms, or an alternate range, such as 2 to 8 carbons, or 2 to 6 carbons, and the like, and one or more carbon-carbon double bond (a.k.a. pi-bond). Illustrative alkenyl groups include, but are not limited to, vinyl, propenyl, isopropenyl, 1-butenyl, 2-butenyl, isobutenyl, 1-pentenyl, 2-pentenyl, and the like. It will be appreciated that an alkenyl group can be unsubstituted or substituted as described herein. An alkenyl group can be substituted with any of the substituents in the various embodiments described herein, including one or more of such substituents.

As used herein, the term "alkynyl" includes a chain of carbon atoms, which is optionally branched, contains from 2 to 20 carbon atoms, or an alternate range, such as 2 to 8 carbons, or 2 to 6 carbons, and the like, and one or more carbon-carbon triple bond. Illustrative alkynyl groups include, but are not limited to, acetylenyl, propynyl, 1-butynyl, 2-butynyl, 1-pentynyl, 2-pentynyl, and the like. It will be appreciated that an alkynyl group can be unsubstituted or substituted as described herein. An alkynyl group can be substituted with any of the substituents in the various embodiments described herein, including one or more of such substituents.

As used herein, the term "aryl" refers to a mono-valent all-carbon monocyclic or fused-ring polycyclic group having from 6 to 14 carbon atoms ($C_6$-$C_{14}$ aryl), or alternatively from 6 to 10 carbon atoms ($C_6$-$C_{10}$ aryl), and a completely conjugated pi-electron system. Examples, without limitation, of aryl groups are phenyl, naphthyl and anthracenyl. It will be appreciated that an aryl group can be unsubstituted or substituted as described herein. An aryl group can be substituted with any of the substituents in the various embodiments described herein, including one or more of such substituents.

DETAILED DESCRIPTION

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms “a,” “an,” and “the” include plural referents unless the context clearly dictates otherwise. It is further noted that the claims may be drafted to exclude any optional element. As such, this statement is intended to serve as antecedent basis for use of such exclusive terminology as “solely,” “only” and the like in connection with the recitation of claim elements, or use of a “negative” limitation.

Representative Embodiments

Described herein is a carbon efficient approach to synthesize nicotinic acid derivatives, such as 2-trifluoromethylnicotinic acid, starting from trifluoro-acetoacetate derivatives, such as ethyl trifluoro-acetoacetate and vinylaldehyde derivatives, such as acrolein. The processes described herein provide novel dihydropyran derivatives that are useful in the preparation of nicotinic acid derivatives by further transformation. According to the processes of the disclosure, the dihydropyran derivative is readily converted in a second step to a pyridine ester derivative by reacting with a nitrogen source additive, such as ammonium acetate in presence of an oxidizing agent. Finally in a third step, ester hydrolysis of the pyridine ester derivative is accomplished using a base under mild conditions to generate the target product nicotinic acid derivative. The processes of the disclosure can be described according to Scheme 1.

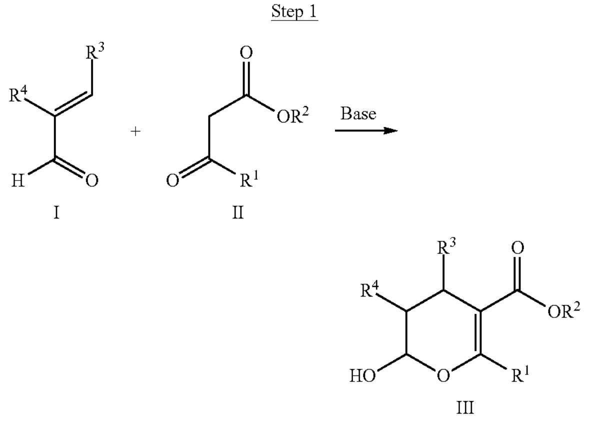

I II III

-continued

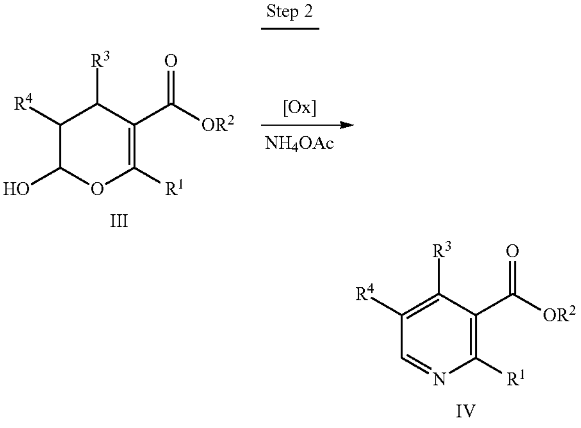

III IV

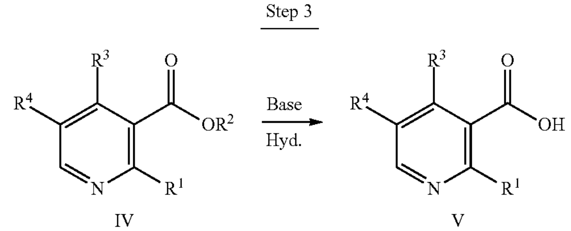

IV V

It will be appreciated that the present disclosure provides processes for preparing a compound of the formula V described in the paragraphs above and below, comprising step (i) and one or more than one of the recited steps (ii) and (iii). Accordingly, the present disclosure provides a process for preparing a compound of the formula V, comprising step (i). Alternatively, the present disclosure provides a process for preparing a compound of the formula V, comprising steps (i) and (ii). Alternatively, the present disclosure provides a process for preparing a compound of the formula V, comprising steps (i), (ii), and (iii). Alternatively, the present disclosure provides a process for preparing a compound of the formula III, comprising step (ii). Alternatively, the present disclosure provides a process for preparing a compound of the formula IV, comprising steps (i) and (ii).

In step (i), a compound of the formula I

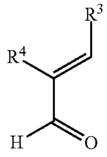
I wherein wherein each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; is contacted with a compound of the formula II

II

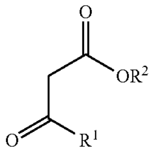

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —O$C_1$-$C_8$ alkyl, —N($C_1$-$C_8$ alkyl$)_2$, or —S$C_1$-$C_8$ alkyl; and $R^2$ is a $C_1$-$C_8$ alkyl; in the presence of a base to provide a compound of the formula III

III

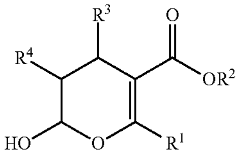

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —O$C_1$-$C_8$ alkyl, —N($C_1$-$C_8$ alkyl$)_2$, or —S$C_1$-$C_8$ alkyl;

$R^2$ is a $C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —O$C_1$-$C_8$ alkyl, —N($C_1$-$C_8$ alkyl$)_2$, or —S$C_1$-$C_8$ alkyl.

In step (i), the base can be any suitable base, such as an organic base or an inorganic base. In some embodiments, the base in step (i) can be an organic base, such as an amine base. Suitable amine bases include, but are not limited to, triethyl amine (TEA), tributyl amine, N,N-diisopropyl ethyl amine (DIPEA), N,N,N',N'-Tetramethyl-1,8-naphthalenediamine, 1,8-diazabicycloundec-7-ene (DBU), 1,5-diazabicyclo(4.3.0)non-5-ene (DBN), and 2,6-di-tert-butylpyridine. Step (i) can be carried out in the presence of an optional solvent. The solvent can be any suitable solvent, such as an organic solvent. In some embodiments, the solvent in step (i) can be an alcohol based solvent. Suitable alcohol based solvents include, but are not limited to, methanol, ethanol, iso-propanol, n-propanol, n-butanol, iso-butanol, tert-butanol, n-pentanol, sec-pentanol, iso-pentanol, ethylene glycol, methyl isobutyl carbinol, and propylene glycol. It will be appreciated that step (i) can be conducted at any temperature commonly used in connection with ring-formation using Michael addition chemistry processes, such as room temperature, under cooling, or under warming conditions. In some embodiments, step (i) can be carried out at a temperature of about 0° C. to about 25° C. In some embodiments, step (i) can be carried out by the addition of the compound of the formula I to the compound of the formula II at a temperature of about 0° C. to about 25° C. In some embodiments, after addition of a compound of the formula I to the compound of the formula II, the reaction can be heated to a temperature above room temperature, such as at the reflux temperature of a solvent used in connection with step (i). In some embodiments, step (i) can be carried out at a temperature of about 60° C. to about 280° C.

In some embodiments of step (i), the compound of the formula I can be acrolein (aka propenal) and the compound of the formula II can be one or more esters of 4,4,4-trifluoro-3-oxobutanoic acid. It will be appreciated that the one or more esters of 4,4,4-trifluoro-3-oxobutanoic acid can be a mixture of $C_1$-$C_8$ alkyl esters of 4,4,4-trifluoro-3-oxobutanoic acid as depicted by the following formula

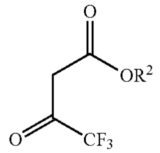

wherein $R^2$ is $C_1$-$C_8$ alkyl. In some embodiments, the product of step (i) when the compound of the formula I is acrolein (aka propenal) and the compound of the formula II is one or more esters of 4,4,4-trifluoro-3-oxobutanoic acid can be described by the formula

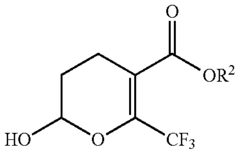

wherein $R^2$ is $C_1$-$C_8$ alkyl.

In step (ii), a compound of the formula III

III

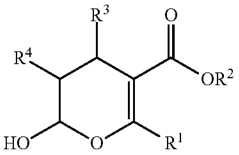

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —O$C_1$-$C_8$ alkyl, —N($C_1$-$C_8$ alkyl$)_2$, or —S$C_1$-$C_8$ alkyl;

$R^2$ is a $C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; can be contacted with oxidizing agent and an additive, such as a nitrogen source additive, to provide a compound of the formula IV

IV

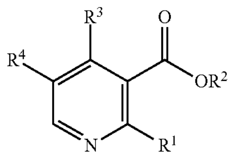

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl;

$R^2$ is a $C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl.

In step (ii), the oxidizing agent can be any suitable oxidizing agent, such as oxygen ($O_2$) in the presence of an optional catalyst. The optional catalyst can be any suitable catalyst, such as a metal catalyst. Suitable metal catalysts include, but are not limited to, copper (I) acetate, copper (I) chloride, copper (I) oxide, manganese (II) acetate, copper (II) acetate, copper (II) chloride, copper (II) oxide, and iron (III) acetate. The additive in step (ii) can be a nitrogen source additive, such as ammonia, ammonium acetate, ammonium hydroxide, ammonium chloride, ammonium carbonate, and ammonium nitrate. It can be advantageous to use the nitrogen source in an equimolar amount relative to the compound of the formula III, or in a molar excess relative to the compound of the formula III. In some embodiments, the nitrogen source, such as ammonium acetate, can be used in a molar excess relative to the compound of the formula III. Step (ii) can be carried out in the presence of an optional solvent. The solvent can be any suitable solvent, such as an organic solvent. In some embodiments, the solvent in step (ii) can be an alcohol based solvent. Suitable alcohol based solvents include, but are not limited to, methanol, ethanol, iso-propanol, n-propanol, n-butanol, iso-butanol, tert-butanol, n-pentanol, sec-pentanol, iso-pentanol, ethylene glycol, methyl isobutyl carbinol, and propylene glycol. It will be appreciated that step (ii) can be conducted at any temperature commonly used in connection with oxidation chemistry processes, such as room temperature, under cooling, or under warming conditions. In some embodiments, step (ii) can be heated to a temperature above room temperature, such as at the reflux temperature of a solvent used in connection with step (ii). In some embodiments, step (ii) can be carried out at a temperature of about 60° C. to about 280° C. The compound of the formula IV can be purified, for example by steam distillation, or the compound of the formula IV can be carried on in further synthesis without purification.

In some embodiments of step (ii), the compound of the formula III can be of the formula

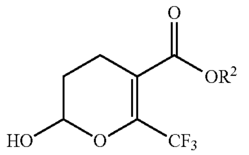

wherein $R^2$ is a $C_1$-$C_8$ alkyl, and the product compound of the formula IV can be

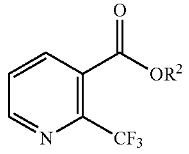

wherein $R^2$ is a $C_1$-$C_8$ alkyl.

In step (iii), a compound of the formula IV

IV

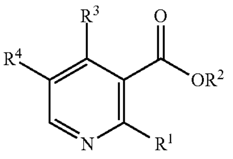

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl;

$R^2$ is a $C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl; can be contacted with a base to provide a compound of the formula V

V

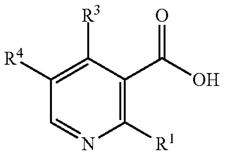

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl;

$R^2$ is a $C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl.

In step (iii), the base can be any suitable base, such as an organic base or an inorganic base. In some embodiments, the base in step (iii) can be an inorganic base, such as a hydroxide base. Suitable hydroxide bases include, but are not limited to, sodium hydroxide, lithium hydroxide, potassium hydroxide, cesium hydroxide, calcium hydroxide, barium hydroxide, sodium carbonate, ammonium hydroxide, and mangnesium hydroxide. In some embodiments, the base can be sodium hydroxide. In some embodiments, the base can be a 25% solution of sodium hydroxide. Step (iii) can be carried out in the presence of an optional solvent. The solvent can be any suitable solvent, such as an organic solvent. In some embodiments, the solvent in step (iii) can be an alcohol based solvent. Suitable alcohol based solvents include, but are not limited to, methanol, ethanol, isopropanol, n-propanol, n-butanol, iso-butanol, tert-butanol, n-pentanol, sec-pentanol, iso-pentanol, ethylene glycol, methyl isobutyl carbinol, and propylene glycol. It will be appreciated that step (iii) can be conducted at any temperature commonly used in connection with oxidation chemistry processes, such as room temperature, under cooling, or under warming conditions. In some embodiments, step (iii) can be carried out at a lower temperature by using a hydroxide base solution that is in a concentration range of from about 10% hydroxide base to about 40% hydroxide base. In some embodiments, step (i) can be carried out at a temperature of about 0° C. to about 25° C. In some embodiments, the reaction is cooled to below room temperature, at a temperature of about 0° C. to about 25° C. and the base is added to the cooled reaction, which is allowed to warm to room temperature after addition is complete. It will be appreciated that the base hydrolysis reaction can be stopped and the product isolated by acidifying the reaction with, for example a solution of an inorganic acid (e.g. sulfuric acid), followed by filtering the final product.

In some embodiments of step (iii), the compound of the formula IV can be of the formula

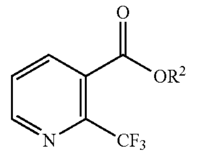

wherein $R^2$ is a $C_1$-$C_8$ alkyl.

In some embodiments, the disclosure provides a compound of the formula III

III

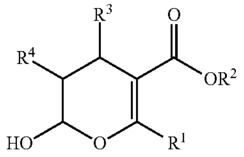

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl;

$R^2$ is a $C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, —$OC_1$-$C_8$ alkyl, —$N(C_1$-$C_8$ alkyl$)_2$, or —$SC_1$-$C_8$ alkyl.

In some embodiments, $R^1$ is methyl, trifluoromethyl, or difluoromethyl. In some embodiments, $R^4$ is H, methyl, ethyl, n-propyl, i-propyl, or allyl. In some embodiments, $R^3$ is H, methyl, ethyl, n-propyl, i-propyl, or allyl. In some embodiments, $R^2$ is methyl, ethyl, n-propyl, or i-propyl. In some embodiments, the compound of the formula III is selected from the group consisting of

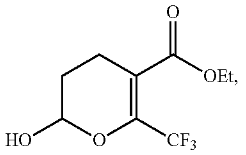
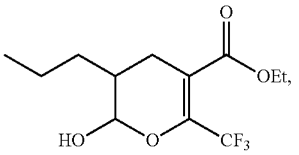
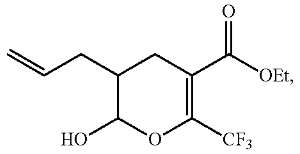
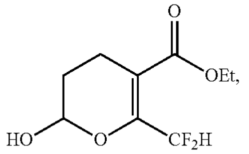
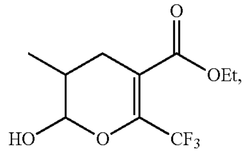
and
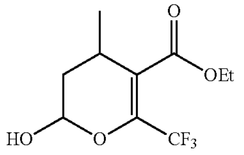

EXAMPLES

The examples and preparations provided below further illustrate and exemplify particular aspects of embodiments of the disclosure. It is to be understood that the scope of the present disclosure is not limited in any way by the scope of the following examples.

Example 1

Step 1—Ethyl 2-hydroxy-6-(trifluoromethyl)-3,4-dihydro-2H-pyran-5-carboxylate:

Methanol (200 mL) and ethyl trifluoro-acetoacetate (37.0 g, 0.199 mol) charged to a pot and stirred and kept below 5-10° C. Triethylamine (2.1 g, 0.021 mol) was added followed by a solution of acrolein (11.6 g, 0.201 mol) in methanol (50 mL) was added over 1 h and the whole mixture stirred for 35 min at 23° C. The reaction mixture is directly used in step 2. On stripping the solvent the product is obtained as a liquid with amber color. The characterization has been done using GCMS Mw 240 and Fluorine NMR (−85.8 ppm).

Step 2—Ethyl 2-(trifluoromethyl)nicotinate:

Ammonium acetate (30.8 g, 0.400 mol) and copper acetate monohydrate (4.1 g, 0.021 mol) were charged to the above reaction mixture and heated reflux (67° C.) while introducing oxygen (50%) subsurface. Water (100 mL) added to increase reflux temperature to 73° C. Progress of the reaction was followed by NMR. The product was isolated by steam distillation with all the methanol coming off first followed by the product and water. A 41% yield of the final product was observed. The product could also be isolated using distillation. The product was characterized using GCMS Mw 219 and Fluorine NMR (−75.5 ppm).

Step 3—2-(Trifluoromethyl)nicotinic Acid:

Ethyl 2-(trifluoromethyl)nicotinate (14.6 g, 0.063 mol) and methanol (10 mL) were charged to a pot and cooled to 10-15° C. To this reaction mixture was added sodium hydroxide (25%, 11.4 g, 0.071 mol) over five min. After addition and then stirring at 25° C. for 1 h. The reaction mixture was worked up with addition of water (17 g) and sulfuric acid (3.7 g) to pH 2. After stirring for 30 min the product was isolated by filtration and washed with water (3×20 mL), dried and gave the final product 2-(trifluoromethyl)nicotinic acid in 85% yield. Proton NMR (acetone-d6) 8.9 (d, 1H), 8.3 (d, 1H), 7.8 (dd, 1H); and Fluorine NMR (−65.2 ppm).

Example 2

5-Propyl-2-trifluoromethyl-nicotinic Acid:

5-Propyl-2-trifluoromethyl-nicotinic acid was prepared according to the methods described in Example 1, except that 2-propyl-acrolein was used in place of acrolein. The final product 5-propyl-2-trifluoromethyl-nicotinic acid was characterized by Proton NMR (Acetone-d6) 8.7 (s, 1H), 8.1 (s, 1H), 2.7 (t, 2H), 1.6 (m, 2H), 0.9 (t, 3H); and Fluorine NMR (−62.8 ppm).

Example 3

5-(1-Propenyl)-2-trifluoromethyl-nicotinic Acid:

5-(1-Propenyl)-2-trifluoromethyl-nicotinic acid was prepared according to the methods described in Example 1, except that 2-(2-propenyl)-acrolein in place of acrolein. During the third step of the hydrolysis of the ester group using sodium hydroxide the double bond in the propenyl group isomerizes from 2-position (2-propenyl) to 1-position (1-propenyl). The final product 5-(1-propenyl)-2-trifluoromethyl-nicotinic acid was characterized by Proton NMR (Acetone-d6) 8.8 (s, 1H), 8.2 (s, 1H), 6.7-6.5 (m, 2H), 1.9 (d, 3H); and Fluorine NMR (−62.8 ppm).

What is claimed is:

1. A compound selected from the group consisting of

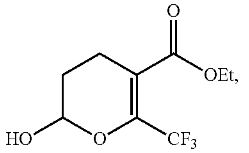
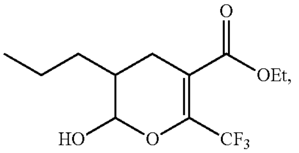
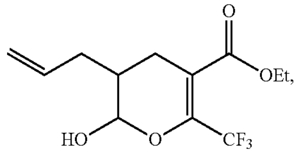
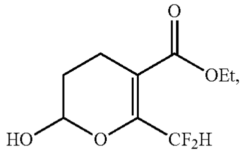
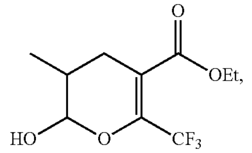
and
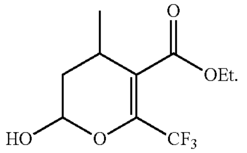

2. A process for preparing a compound of the formula

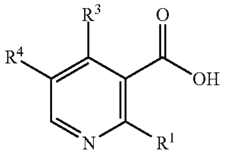

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bronco, $OC_1C_8$ alkyl, —N($C_1$-$C_8$ alkyl)$_2$, or $SC_1C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, $OC_1C_8$ alkyl, —N($C_1$-$C_8$ alkyl)$_2$, or $SC_1C_8$ alkyl;

comprising i. contacting a compound of the formula

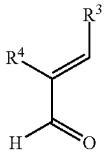

wherein each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bronco, $OC_1C_8$ alkyl, —N($C_1$-$C_8$ alkyl)$_2$, or $SC_1C_8$ alkyl; with a compound of the formula

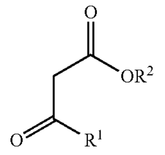

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, $OC_1C_8$ alkyl, —$N(C_1$-$C_8$ alkyl$)_2$, or $SC_1C_8$ alkyl; and $R^2$ is a $C_1$-$C_8$ alkyl; in the presence of a base to provide a compound of the formula

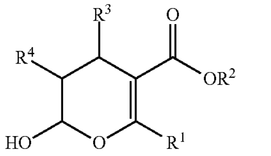

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bronco, $OC_1C_8$ alkyl, —$N(C_1$-$C_8$ alkyl$)_2$, or $SC_1C_8$ alkyl;

$R^2$ is a $C_1$-$C_8$ alkyl; and each of $R^3$ and $R^4$ is independently selected front the group consisting of H, deuterium, $C_1C_8$ alkyl, $C_2$-$C_8$ alkenyl, $C_2$-$C_8$ alkynyl, and $C_6$-$C_{10}$ aryl, wherein each hydrogen atom in $C_1C_8$ alkyl, $C_2$-$C_8$ alkenyl, $C_2$-$C_8$ alkynyl, or $C_6$-$C_{10}$ aryl is independently optionally substituted with deuterium, fluoro, chloro, promo, $OC_1$ $C_8$ alkyl, —$N(C_1$-$C_8$ alkyl$)_2$, or $SC_1C_8$ alkyl.

3. A process for preparing a compound of the formula

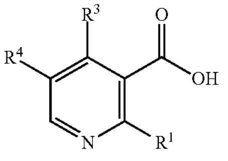

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, $OC_1C_8$ alkyl, —$N(C_1$-$C_8$ alkyl$)_2$, or $SC_1C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, $OC_1C_8$ alkyl, —$N(C_1$-$C_8$ alkyl$)_2$, or $SC_1C_8$ alkyl;

comprising ii. contacting a compound of the formula

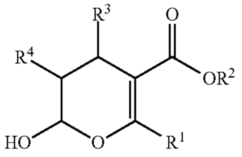

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ an is independently optionally substituted with deuterium, fluoro, chloro, bromo, $OC_1C_8$ alkyl, —$N(C_1$-$C_8$ alkyl$)_2$, or $SC_1C_8$ alkyl;

$R^2$ is a $C_1$-$C_8$ alkyl; and each of $R^3$ and $R^4$ is independently selected front the group consisting of H, deuterium, $C_1$-$C_8$ alkyl, $C_2$ -$C_8$ alkenyl, $C_2$ -$C_8$ alkynyl, and $C_6$-$C_{10}$ aryl, wherein each hydrogen atom in $C_1C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, $OC_1C_8$ alkyl, —$N(C_1$-$C_8$ alkyl$)_2$, or $SC_1C_8$ alkyl; with an oxidizing agent and an additive to provide a compound of the formula

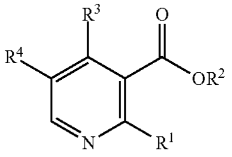

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, $OC_1C_8$ alkyl, —$N(C_1$-$C_8$ alkyl$)_2$, or $SC_1C_8$ alkyl;

$R^2$ is a $C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, $OC_1C_8$ alkyl, —$N(C_1$-$C_8$ alkyl$)_2$, or $SC_1C_8$ alkyl.

4. The process of claim 2, further comprising iii. contacting the compound of the formula

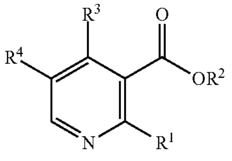

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, $OC_1C_8$ alkyl, —$N(C_1$-$C_8$ alkyl$)_2$, or $SC_1C_8$ alkyl;

$R^2$ is a $C_1$-$C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, $OC_1C_8$ alkyl, —$N(C_1$-$C_8$ alkyl$)_2$, or $SC_1C_8$ alkyl; with a base to provide a compound of the formula

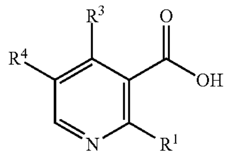

wherein $R^1$ is selected from the group consisting of $C_1$-$C_8$ alkyl, $C_2$-$C_8$ alkenyl, $C_2$-$C_8$ alkynyl, and $C_6$-$C_{10}$ aryl, wherein each hydrogen atom in $C_1$-$C_8$ alkyl, $C_2$-$C_8$ alkenyl, $C_2$-$C_8$ alkynyl, or $C_6$-$C_{10}$ aryl is independently optionally substituted with deuterium, fluoro, chloro, bronco, $OC_1C_8$ alkyl, —$N(C_1$-$C_8$ alkyl$)_2$, or $SC_1C_8$ alkyl; and each of $R^3$ and $R^4$ is independently selected from the group consisting of H, deuterium, $C_1$-$C_8$ alkyl, $C_2$-$C_8$ alkenyl, $C_2$-$C_8$ alkynyl, and $C_6$-$C_{10}$ aryl, wherein each hydrogen atom in $C_1C_8$ alkyl, $C_2$-$C_8$ alkenyl, $C_2$-$C_8$ alkynyl, or $C_6$-$C_{10}$ aryl is independently optionally substituted with deuterium, fluoro, chloro, bromo, $OC_1C_8$ alkyl, —$N(C_1$-$C_8$ alkyl$)_2$, or $SC_1C_8$ alkyl.

5. The process of claim 4, wherein the base in step (i) is an organic base.

6. The process of claim 5, wherein the base in step (i) is an amine base.

7. The process of any one of claim 6, wherein the base in step (i) is selected from the group consisting of triethyl amine (TEA), tributyl amine, N,N-diisopropyl ethyl amine (DIPEA), N,N,N',N'-Tetramethyl-1,8-naphthalenediamine, 1,8-diazabicycloundec-7-ene (DBU), 1,5-diazabicyclo (4.3.0)non-5-ene (DBN), and 2,6-di-tert-butylpyridine.

8. The process of claim 4, wherein step (i) is carried out in the presence of an alcohol solvent.

9. The process of claim 8, wherein the organic solvent step (i) is selected from the group consisting of methanol, ethanol, iso-propanol, n-propanol, n-butanol, iso-butanol, tert-butanol, n-pentanol, sec-pentanol, iso-pentanol, ethylene glycol, methyl isobutyl carbinol, and propylene glycol.

10. The process of claim 4, wherein step (i) is carried out by that addition of acrolein to ethyl trifluoro-acetoacetate at a temperature of about 0° C. to about 25° C.

11. The process of claim 4, wherein the oxidizing agent in step (ii) is $O_2$ in the presence of a metal catalyst.

12. The process of claim 11, wherein the metal catalyst is selected from the group consisting of copper (I) acetate, copper (I) chloride, copper (I) oxide, manganese (II) acetate, copper (II) acetate, copper (II) chloride, copper (II) oxide, and iron (III) acetate.

13. The process of claim 4, wherein the additive in step (ii) is selected from the group consisting of ammonium acetate, ammonium hydroxide, ammonium chloride, ammonium carbonate, and ammonium nitrate.

14. The process of claim 4, wherein step (ii) is carried out in an alcohol solvent.

15. The process of claim 14, wherein the organic solvent step (ii) is selected from the group consisting of methanol, ethanol, iso-propanol, n-propanol, n-butanol, iso-butanol, tert-butanol, n-pentanol, sec-pentanol, iso-pentanol, ethylene glycol, methyl isobutyl carbinol, and propylene glycol.

* * * * *